United States Patent [19]
Sorce et al.

[11] 3,952,335
[45] Apr. 27, 1976

[54] LARYNGEAL PROSTHESIS

[75] Inventors: Peter S. Sorce, Tonawanda; Earl W. Clifford, Getzville, both of N.Y.

[73] Assignee: The Aro Corporation, Bryan, Ohio

[22] Filed: Sept. 25, 1974

[21] Appl. No.: 509,262

[52] U.S. Cl. .................................... 3/1.3; 128/351
[51] Int. Cl.² ............................................ A61F 1/20
[58] Field of Search ........................ 3/1.3; 128/351

[56] References Cited
UNITED STATES PATENTS

| | | | |
|---|---|---|---|
| 2,804,076 | 8/1957 | Giraudon | 128/351 |
| 3,747,127 | 7/1973 | Taub | 3/1.3 |

*Primary Examiner*—Ronald L. Frinks
*Attorney, Agent, or Firm*—Sommer & Sommer

[57] ABSTRACT

A laryngeal prosthesis for a post-laryngectomy patient includes a control valve, a fitting, and a conduit operatively communicating the control valve and fitting. The control valve has a housing defining a chamber therewithin. The housing is provided with a tracheal opening adapted to communicate with the patient's trachea through a tracheal fistula, a diversion opening, and a control opening surrounded by an internal seat. A flapper is arranged within the housing to move toward and away from the seat. The fitting includes an inlet opening and an outlet opening adapted to communicate with the patient's hypopharynx through a hypopharyngeal fistula. The conduit communicates the diversion opening with the fitting inlet opening. The prosthesis enables the patient to inhale, exhale and cough through the control opening, and to speak alaryngeally by selectively diverting exhaled air from the tracheal fistula to the hypopharyngeal fistula.

15 Claims, 15 Drawing Figures

LARYNGEAL PROSTHESIS

BACKGROUND OF THE INVENTION

1. Field of the Invention

The present invention relates generally to laryngeal prostheses for enabling alaryngeal speech by a patient whose larynx has been removed.

2. Description of the Prior Art

Human speech is enabled by the passage of expired air from the lungs up through the trachea to pass through the laryngeal cavity and be exhaled through the mouth. The laryngeal cavity contains a plurality of adjustably-tensioned mucous membranes, or vocal cords, stretched thereacross. During such exhalation, these membranes are caused to vibrate and produce audible sounds by a flow of expired air therearound, and differences in pitch are achieved by muscles which adjust the tension of these vibratory membranes.

Since the larynx is susceptible to trauma, injury, and various diseases, a laryngectomy may have to be performed to remove a person's larynx. However, such removal of the larynx also removes the patient's primary sound-producing vibratory elements and therefore sharply reduces the patient's ability to produce coherent audible sounds.

It is known to provide such post-laryngectomy patients with a laryngeal prosthesis by which the flow of expired air may be selectively diverted to an alternate body cavity capable of producing an audible sound. This type of alternative speech is generally referred to as being "alaryngeal" because it enables the patient to produce coherent audible signals similar to those produced by the larynx.

Earlier known attempts to produce such a laryngeal prosthesis have generally contemplated that the flow of expired air be diverted from the trachea to the cervical esophagus. However, this concept has been complicated by the danger of providing a cervical esophageal fistula in the patient's neck due to the risk of rupturing one of the carotid arteries, the problem of saliva leakage, and the general requirement that the patient's neck have not been previously violated by surgery or irradiation.

One example of a prior art laryngeal prosthesis requiring a cervical esophageal fistula is taught by Taub U.S. Pat. No. 3,747,127 which discloses a device having a first tube adapted to be inserted into a tracheal fistula and a second tube adapted to be inserted into a cervical esophageal fistula. A valve arranged between the tubes permits the patient to inhale and exhale through a main port. This valve may be moved in response to increased breathing levels to divert a flow of expired air from the tracheal fistula to the esophageal fistula to enable alaryngeal speech by the patient. However, in addition to the disadvantage of having to provide a cervical esophageal fistula, this device does not appear to enable the patient to cough freely through the main port without manually adjusting the valve.

Additional isolated structural details of other generally pertinent prior art devices may be shown in Capra U.S. Pat. No. 3,066,674, Roberts U.S. Pat No. 2,405,850, Brehm U.S. Pat. No. 2,198,241, Riesz U.S. Pat. No. 2,024,601, McKesson U.S. Pat. No. 1,922,385, Riesz et al. U.S. Pat. No. 1,901,966, Riesz U.S. Pat. No. 1,836,816, Burchett U.S. Pat. No. 1,867,350, and McKesson U.S. Pat. No. 1,633,705.

Desirably a laryngeal prosthesis should enable a patient to freely inhale, exhale and cough, and speak alaryngeally by selectively diverting expired air to an alternate body cavity capable of producing audible vibrations.

SUMMARY OF THE INVENTION

The present invention provides a laryngeal prosthesis for a post-laryngectomy patient surgically provided with a tracheal fistula and a hypopharyngeal fistula, and enables alaryngeal speech by the patient through primary utilization of the hypopharyngeal cavity.

The prosthesis includes a control valve having a housing defining a chamber therewithin and having a flapper. The housing is provided with a tracheal opening adapted to communicate the chamber with the patient's trachea through the tracheal fistula, a diversion opening communicating with the chamber, and a control opening communicating the chamber with ambient atmosphere. The flapper is mounted on the housing within the chamber and is arranged to move toward and away from the control opening to enable the patient to inhale, exhale and cough through the control opening.

The prosthesis also includes a fitting having an outlet opening adapted to communicate with the patient's hypopharyngeal cavity through the hypopharyngeal fistula, and having an inlet opening communicating with the outlet opening.

The prosthesis further includes means, such as a flexible tube, defining a conduit communicating the control valve diversion opening with the fitting inlet opening.

When the patient attempts to inhale, the flapper is moved away from the control opening to enable such inhaled air to pass therethrough. When the patient attempts to exhale, the flapper is moved slightly toward the control opening but permits such exhaled air to pass therethrough. When the patient coughs, the flapper may deform and pass through the control opening to uncover such opening and permit the exhaled air to pass therethrough. When the patient attempts to speak, the flapper is moved toward the control opening to close the control opening and to divert a flow of expired air through the conduit and fitting to the patient's hypopharyngeal cavity to enable alaryngeal speech by the patient.

A marginal portion of the housing about the control opening may provide a seat for the flapper.

The flapper may have a spring portion to urge the flapper to assume a normal unbiased arcuate shape, and have a flexible marginal portion adapted to sealingly engage the seat when the patient attempts to speak and to deform and enable the flapper to pass through the control opening should the patient cough.

The fitting may further include a one-way valve, such as a self-cleaning "duckbill" valve, to permit a normal flow of diverted expired air to pass through the fitting and enter the hypopharyngeal fistula, but to prevent saliva or foreign material from entering the conduit through the fitting.

The housing may be further provided with a plurality of alternate passageways communicating the chamber with the ambient atmosphere in the event the control opening should become closed.

The prosthesis may further include an audible device, such as a whistle, which is adapted to be inserted into the control opening to move the flapper away from the seat and to enable the patient to sound an audible signal.

Accordingly, one object of the invention is to provide a laryngeal prosthesis to enable alaryngeal speech by a laryngectomy patient.

Another object is to provide a laryngeal prosthesis permitting vocal rehabilitation of a laryngectomy patient by enabling rapid restoration of functional alaryngeal speech.

Another object is to provide a laryngeal prosthesis to enable a laryngectomy patient to inhale, exhale, cough and speak without having to manually adjust the prosthesis.

Another object is to provide a simple and inexpensive laryngeal prosthesis.

Still another object is to provide a control valve for a tracheotomy patient to enable the patient to selectively inhale, exhale, cough and talk without having to manually cover a tracheal fistula.

These and other objects and advantages will become apparent from the foregoing and ongoing specification which includes the drawings and the appended claims.

BRIEF DESCRIPTION OF THE DRAWINGS

FIG. 2 is an enlarged perspective exterior view of the laryngeal prosthesis depicted in FIG. 1, this view showing the prosthesis removed from the patient and illustrating the control valve, the fitting, and the means defining a conduit between the control valve and fitting.

FIG. 3 is an enlarged fragmentary horizontal longitudinal sectional view of the control valve, taken generally on line 3—3 of FIG. 2 and illustrating, in central cross-section, the three-part housing, the chamber within the housing, the flapper, the control housing, the tracheal opening, and the diversion opening.

FIG. 4 is an enlarged fragmentary vertical front elevational view of the control valve, this view being taken generally on line 4—4 of FIG. 2 and principally illustrating the control opening and the internal flapper in exterior elevation.

DESCRIPTION OF THE PREFERRED EMBODIMENT

Figure 1:
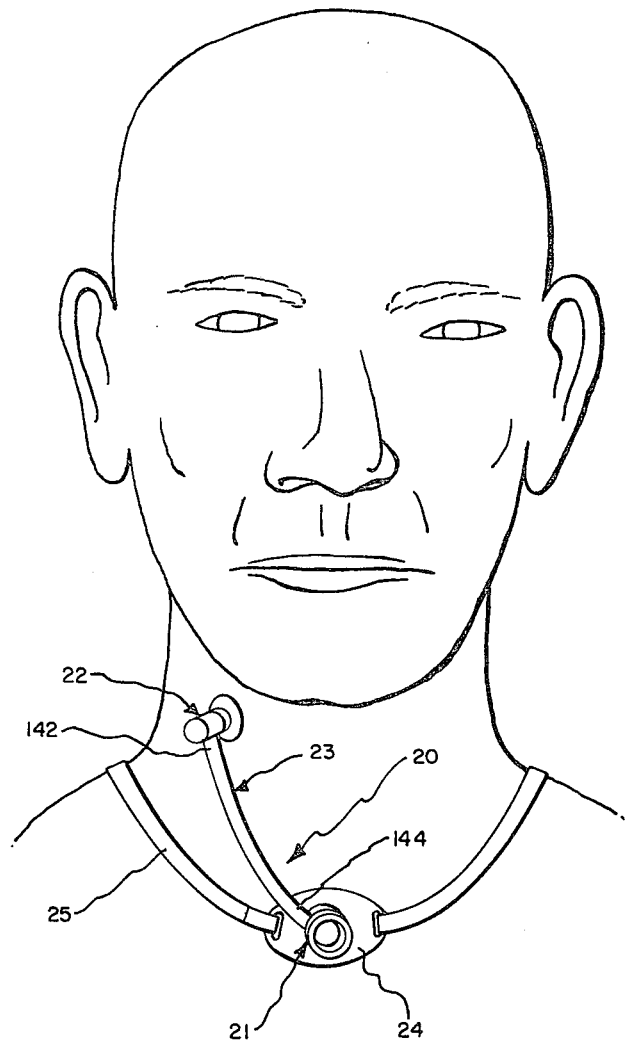
FIG. 1 is a front elevational view of a post-laryngectomy patient wearing the inventive laryngeal prosthesis about his neck, this view illustrating the control valve operatively inserted into the tracheal fistula, the fitting operatively inserted into the hypopharyngeal fistula, and the conduit operatively communicating the control valve and fitting.
Figure 5:
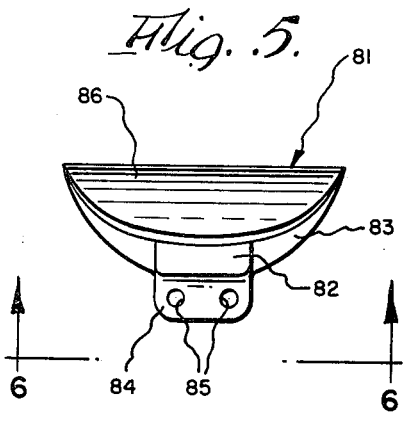
FIG. 5 is a greatly enlarged front elevational view of the flapper principally illustrating the marginal and spring portions thereof.

At the outset, it should be clearly understood that like reference numerals are intended to identify the same elements and/or structure throughout the several drawing figures, as such elements and/or structure may be further described or explained by the entire written specification of which this detailed description is an integral part.

As used herein, the expression "laryngeal prosthesis" is intended to generally refer to a mechanical device enabling alaryngeal speech by a patient whose larynx has been totally or partially removed, and the word "fistula" is intended to broadly refer to an abnormal body opening without limitation of size, depth, or configuration, and may be modified by a suitable adjective. Hence, a "tracheal fistula" is an abnormal body opening communicating with a patient's trachea, and a "hypopharyngeal fistula" is an abnormal body opening communicating with the patient's hypopharyngeal cavity.

Referring initially to FIG. 1, the laryngeal prosthesis, generally indicated at 20, is shown mounted on the neck of a post-laryngectomy human patient who has been surgically provided with a central forward tracheal fistula communicating with the patient's trachea, and a lateral hypopharyngeal fistula communicating with the patient's hypopharyngeal cavity. In actual use, the prosthesis 20 may be concealed by an ascot, if desired.

As conjunctively illustrated in FIGS. 1 and 2, the laryngeal prosthesis 20 broadly includes a control valve 21 arranged proximate the tracheal fistula; a fitting 22 arranged proximate the hypopharyngeal fistula; and means, indicated at 23, defining a conduit operatively communicating the control valve with the fitting. As best shown in FIG. 1, the control valve 21 may be mounted through a surgical plate 24 suitably positioned with respect to the tracheal fistula by an encircling neck strap 25.

Control Valve 21

In FIGS. 2, 3 and 4, the control valve 21 is depicted as including a housing having, from left to right in FIG. 3, a horizontally-elongated tubular left part 26, a larger diameter tubular intermediate part 28, and a right end cap 29.

As best shown cross-sectionally in FIG. 3, the housing left part 26 has an annular vertical left end face 30; a larger diameter annular vertical right end face 31; an inner surface sequentially including, from left to right, a leftward cylindrical surface 32 extending rightwardly from left end face 30, a rightwardly-divergent frusto-conical surface 33, a cylindrical surface 34, a leftwardly-facing annular vertical shoulder 35, and a cylindrical surface 36 continuing rightwardly from shoulder 35 to right end face 31; and an outer surface sequentially including, from left to right, a rightwardly-divergent frusto-conical surface 38 extending rightwardly from left end face 30, a rightwardly-facing annular vertical shoulder 39, a cylindrical surface 40, a rightwardly-divergent frusto-conical surface 41, and a cylindrical surface 42 terminating at right end face 31. Hence, the left end of housing left part 26 is provided with an external tapered plug 43 arranged to be inserted into the tracheal fistula, and the right end is provided with a radially-extending internal annular boss 44 for a purpose hereafter explained. Plug 43 may be inserted directly into the tracheal fistula, or may be inserted into another tube suitably inserted into the patient's trachea.

The housing intermediate part 28 has an annular vertical left end face 45; an annular vertical right end face 46; an inner surface sequentially including, from left to right in FIG. 3, a cylindrical surface 48 extending rightwardly from left end face 45, a rightwardly-facing annular vertical shoulder 49, and a larger diameter cylindrical surface 50 continuing rightwardly and terminating at right end face 46; and an outer surface sequentially including, from left to right, a cylindrical surface 51 extending rightwardly from left end face 45, a rightwardly-facing annular vertical shoulder 52, a cylindrical surface 53, a leftwardly-facing annular vertical shoulder 54, and a cylindrical surface 55 continuing rightwardly and terminating at right end face 46. Hence, this housing intermediate part 28 is provided with an external radially-extending annular groove, bounded by facing shoulders 52, 54 and intermediate cylindrical surface 53, adjacent its left end, which groove is adapted to receive the annular boss 44 of the housing left part 26 when the control valve is assembled.

The housing end cap 29 has an annular vertical left end face 56; an annular vertical right end face 58; an inner surface sequentially including, from left to right in FIG. 3, a cylindrical surface 59 extending rightwardly from left end face 56, a leftwardly-facing annular vertical shoulder 60, a rightwardly-convergent frusto-conical inclined inner surface 61, a cylindrical surface 62, and a rightwardly-divergent frusto-conical inclined outer surface 63 terminating at right end face 58; and an outer surface sequentially including, from left to right, a cylindrical surface 64 extending rightwardly from left end face 56, and a chamfered surface 65 adjacent the right end of the cap 29 and joining outer surface 64 and right end face 58. Adjacent its right end, end cap 29 is further provided with a plurality of radial passageways 67 extending between outer surface 64 and inner surfaces 62, 63. These radial passageways function to provide an alternative means for communicating the control opening with ambient atmosphere. Hence, should the control opening 80 become blocked, as by a patient's ascot covering the control opening, the radial passageways will provide an alternative passageway to permit air to be inhaled through the control valve. Hence, the housing end cap 29 may be assembled on the right end portion of housing intermediate part 28 so that the end cap inner surface 59 is arranged to face intermediate part outer cylindrical surface 55. When so assembled an exposed inner annular marginal portion of end cap shoulder 60 around the control opening will provide a seat 60' for the flapper, as later described.

Still referring to FIG. 3, the housing intermediate part 28 is shown further provided with an externally recessed or countersunk radial through hole 66 in which an external nipple 68 is suitably mounted. This nipple 68 is shown as having a lower annular horizontal end face 69 arranged to suitably engage the recessed upwardly-facing annular shoulder 70 encircling hole 66; an upper annular horizontal end face 71; a through-bore bounded by an inner cylindrical surface 72; and an outer surface sequentially including a downwardly-divergent frusto-conical surface 73 extending downwardly from upper end face 71, a downwardly-facing horizontal annular shoulder 74, and a cylindrical surface 75 continuing downwardly and terminating at lower end face 69. Hence, the upper end of nipple 68 is provided with an external tapered plug 76, and the lower end of this nipple is adapted to fit within the recess surrounding through hole 66.

The control valve 21 thus includes housing formed by assembling housing left part 26, housing intermediate part 28, and housing end cap 29 together in the manner heretofore described, this housing defining a chamber 77 therewithin and provided with a leftward tracheal opening 78 communicating with the chamber, a radial diversion outlet 79 communicating with the chamber through nipple 68, and a rightward control opening 80 communicating the chamber with the ambient atmosphere through end cap 29. Still referring to FIG. 3, the control valve is shown as further including a flapper, generally indicated at 81, mounted on the housing in the chamber and adapted to move toward and away from control opening 80 to enable the patient to inhale, exhale and cough therethrough.

Flapper 81

Referring now collectively to FIGS. 5–8, flapper 81 is shown as being an arcuate member having a central spring portion 82 and an outer marginal flexible portion 83. The convex face of flapper 81 may be visualized as having a circular outline, if pressed flat, wrapped around a cylindrical surface of revolution, the spring portion 82 being arranged on the concave underside of the arcuate structure so formed. The thickened spring portion 82 appears as an elongated rectangular member, when viewed in bottom plan (FIG. 6), having a left end marginal mounting portion 84 of reduced thickness (FIG. 7) continuing tangentially beyond the contour of the flexible portion and provided with a pair of spaced through holes 85 by which the flapper may be mounted on the housing. This flapper may be preferably formed of silicone and may be configured to have the area of its convex upper surface 86 be about 1.91 times the area of the annular housing seat 60'. The marginal portion 83 is of reduced thickness so as to be flexible and to sealingly assume the contour of the seat when the patient attempts to speak, and to deform sufficiently to pass through the control opening 80 should the patient cough. The spring portion 82 functions to continuously urge the flapper to assume the normal arcuate shape depicted in FIGS. 5–8 regardless of whether an overcoming force displaces the flapper toward or away from the control opening 80, as later described.

Because respiratory characteristics vary widely from patient to patient, it is impractical to describe the flapper as having a universally acceptable degree of flexibility or a specified spring rate. Rather, the flapper should be custom-fitted to the particular patient so that the patient may exercise the inhalation, exhalation, talking and coughing modes at inspiration and expiration pressures which are comfortable to the patient. However, to appreciate the magnitudes of air pressure inhaled or exhaled during the several modes, an average patient may typically inhale and exhale at a pressure of about 4 centimeters of water, talk at a pressure of about 8 centimeters of water, and cough at a pressure of about 50 centimeters of water.

Figures 6, 7, 8:
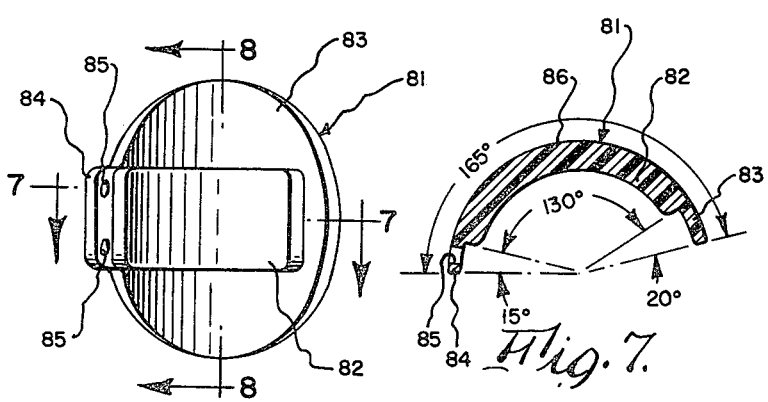
FIG. 6 is a bottom plan view of the flapper, this view being taken generally on line 6—6 of FIG. 5 and showing the concave underside of the flapper and illustrating the marginal and spring portions of the flapper.
FIG. 7 is a longitudinal horizontal sectional view thereof taken centrally through the flapper spring portion on line 7—7 of FIG. 6 illustrating the spring and marginal portions of the flapper in longitudinal cross-section.
FIG. 8 is a transverse vertical sectional view thereof taken centrally through the flapper on line 8—8 of FIG. 6 and illustrating the spring and marginal portions of the flapper in transverse cross-section.

In FIG. 7, the convex upper surface 86 of the flapper is shown as lying in an arc of about 165°; and the concave lower surface of the flapper is shown as including, from left to right, the mounting portion 84 lying in an arc of about 15°, the spring portion 82 lying in an arc of about 130°, and the marginal portion 83 continuing therebeyond and lying in an arc of about 20°. In FIG. 8, the marginal portion 83 is shown as having a nominal thickness ($t$) equal to about 0.23 times the radius of flapper curvature, and the spring portion 82 is shown as having a greater thickness (T) equal to about 0.25 times this radius of curvature. However, it should be clearly understood that these dimensions are intended to be exemplary only and are not to be construed as limiting the claims unless expressly incorporated therein.

Figure 10:
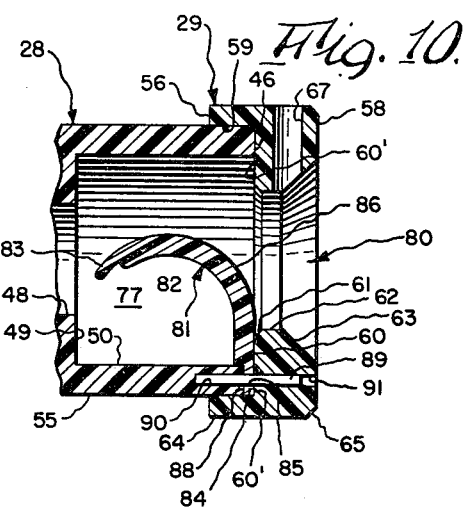
FIG. 10 is a fragmentary sectional view of the control valve, taken generally on line 10—10 of FIG. 4 and illustrating the normal unbiased position of the flapper in transverse cross-section.

As best shown in FIG. 10, the flapper mounting portion 84 may be arranged in a recessed rectangular slot 88 extending leftwardly into intermediate housing part 28 from the right end face 46 thereof, and is maintained in this position by pins 89 having intermediate portions passed through flapper holes 85, their left end portions suitably pressed into a pair of aligned holes 90 provided in the intermediate housing part 28 from the right end thereof, and their rightward end portions suitably arranged in a pair of aligned holes 91 provided through the housing end cap 29.

Fitting 22

Figure 9:
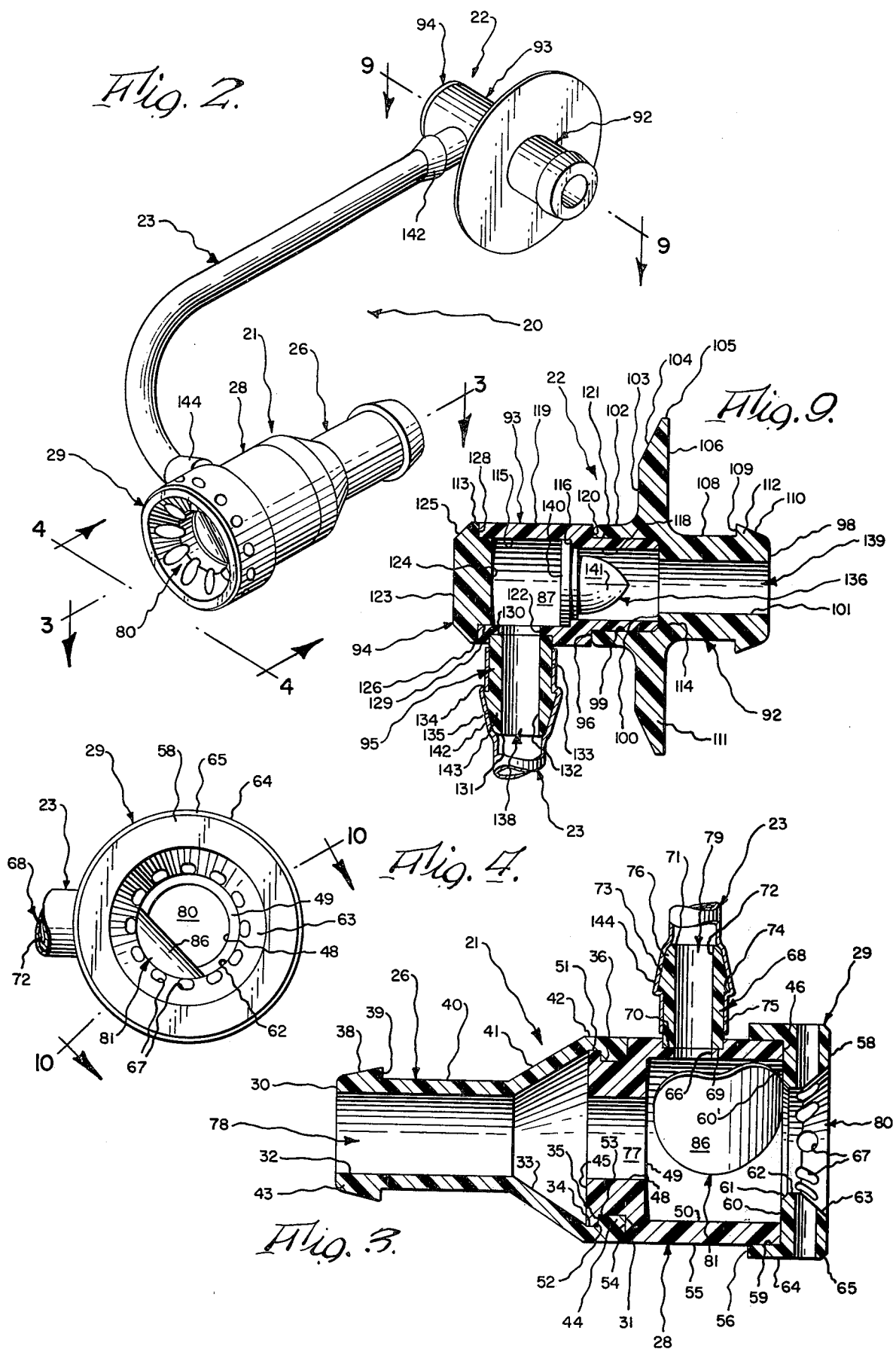
FIG. 9 is an enlarged fragmentary horizontal longitudinal sectional view of the fitting, taken generally on line 9—9 of FIG. 2 and illustrating the fitting in central cross-section, the inlet opening communicating with the conduit, the outlet opening adapted to be inserted into the hypopharyngeal fistula, and the one-way duckbill valve arranged within the fitting.

Adverting now to FIG. 2, the laryngeal prosthesis 20 also includes a fitting 22. As best shown in FIG. 9, fitting 22 includes a right mounting part 92, an intermediate body part 93, a left end plug 94, and a nipple 95.

As best shown in FIG. 9, the fitting mounting part 92 has an annular vertical left end face 98; an annular vertical right end face 98; a central horizontal through-bore bounded by an inner surface sequentially including, from left to right, a cylindrical surface 99 extending rightwardly from left end face 96, a leftwardly-facing annular vertical shoulder 100, and a cylindrical surface 101 continuing rightwardly and terminating at right end face 98; and an outer surface sequentially including, from left to right, a cylindrical surface 102 extending rightwardly from left end face 96, a large diameter leftwardly-facing annular vertical shoulder 103, a rightwardly-divergent frusto-conical surface 104, a cylindrical surface 105, a large diameter rightwardly-facing annular vertical shoulder 106, a cylindrical surface 108, a leftwardly-facing annular vertical shoulder 109, and a rightwardly-convergent frusto-conical surface 110 continuing rightwardly and terminating at right end face 98. Hence, this fitting mounting part 92 is provided with an intermediate external large diameter radially-extending annular flange 111, and an external tapered plug 112 adjacent its right end, which plug 112 is adapted to be inserted into the hypopharyngeal fistula.

The fitting intermediate body part 93 is shown as having an annular vertical left end face 113; an annular vertical right end face 114; a central horizontal through-bore bounded by an inner surface sequentially including, from left to right in FIG. 9, a cylindrical surface 115 extending rightwardly from left end face 113, a leftwardly-facing annular vertical shoulder 116, and a cylindrical surface 118 continuing rightwardly and terminating at right end face 114; and an outer surface sequentially including, from left to right, a cylindrical surface 119 extending rightwardly from left end face 113, a rightwardly-facing annular vertical shoulder 120, and a cylindrical surface 121 continuing rightwardly and terminating at right end face 114. Moreover, fitting body part 93 is further provided with an externally recessed or countersunk radial through hole 122 between inner surface 115 and outer surface 119, which hole 122 is adapted to receive fitting nipple 95. This right end portion of fitting body part 93 may be inserted into the left end portion of fitting mounting part 92 such that fitting body part surfaces 120, 121 and 114 are arranged to face fitting mounting part surfaces 96, 99 and 100, respectively.

The fitting left end plug 94 is shown as having a circular vertical left end face 123; a larger diameter circular vertical right end face 124; and an outer surface sequentially including a rightwardly-divergent frusto-conical surface 125 extending rightwardly from left end face 123, a cylindrical surface 126, a rightwardly-facing annular vertical shoulder 128, and a cylindrical surface 129 continuing rightwardly and terminating at right end face 124. Hence, the right end portion of fitting end plug 94 may be inserted into the left end portion of fitting body part 93 such that end plug surfaces 128 and 129 are arranged to face body part surfaces 113 and 115, respectively. Accordingly, this end plug 94 functions to removably close the open left end of the fitting intermediate part 93 and to define a chamber 87 within the fitting.

The fitting nipple 95 is shown as having an upper annular horizontal end face 130, a lower annular horizontal end face 131; a vertical through-bore bounded by inner cylindrical surface 132; and an outer surface sequentially including a cylindrical surface 133 extending downwardly from upper end face 130, an upwardly-facing annular horizontal shoulder 134, and a downwardly-divergent frusto-conical surface 135 continuing downwardly and terminating at lower end face 131. The upper end portion of fitting nipple 95 may be inserted into the externally countersunk hole 122 of the fitting body part 93 in a manner such that fitting 68 is inserted into control valve intermediate part 28. In this connection, such nipple may be cemented in position, or frictionally press-fitted, or otherwise suitably mounted on its support.

Still referring to FIG. 9, a one-way valve 136 is arranged within the fitting body part 93 and functions to permit a normal flow of expired air entering the fitting through fitting inlet opening 138 to pass through the fitting and exit via fitting outlet opening 139. However, since fitting right end plug 112 is adapted to be inserted into the patient's hypopharyngeal fistula, this one-way valve 136 also operates to prevent saliva or other foreign matter from passing through the fitting 22 and entering the conduit. In the preferred embodiment herein described, this one-way valve 136 is specifically shown as being a self-cleaning high flow duckbill valve having a leftward annular base 140 adapted to engage the inner shoulder 116 of fitting body part 93, and having upper and lower clamshell halves 141, 141 adapted to move pivotally away from one another to enable a normal flow of diverted exhaled air entering the fitting through nipple 95 to pass through the fitting and enter the hypopharyngeal fistula of the patient through fitting outlet opening 139. In the absence of a flow of such diverted exhaled air, clamshell halves 141, 141 move pivotally toward one another to close the passageway through fitting 22 and thereby prevent saliva and foreign material from entering the conduit. If desired, a vibratory element, such as a reed, may be suitably provided in fitting 22 to produce audible vibrations.

Conduit Means 23

Adverting now to FIGS. 1 and 2, the means 23 defining a conduit is shown as being a flexible tube having one end portion 142 fitted over the external tapered plug 143 of fitting nipple 95, and having its other end portion 144 similarily fitted over the external tapered plug 76 of the control valve nipple 68. Hence, this flexible tube 23 defines a passageway or conduit for directing a flow of diverted exhaled air from control valve diversion opening 79 to fitting inlet opening 138.

Operation (FIGS. 10–14)

The several modes of operation of the laryngeal prosthesis 20 are depicted in FIGS. 10–14.

Normal Mode (FIG. 10)

In FIG. 10, the flapper 81 is depicted as being in its normal arcuate unbiased shape, previously illustrated in FIGS 5–8. While the flapper is in this normal position, the control opening 80 is open or uncovered to communicate the control valve chamber 77 with the ambient atmosphere.

Figure 11:
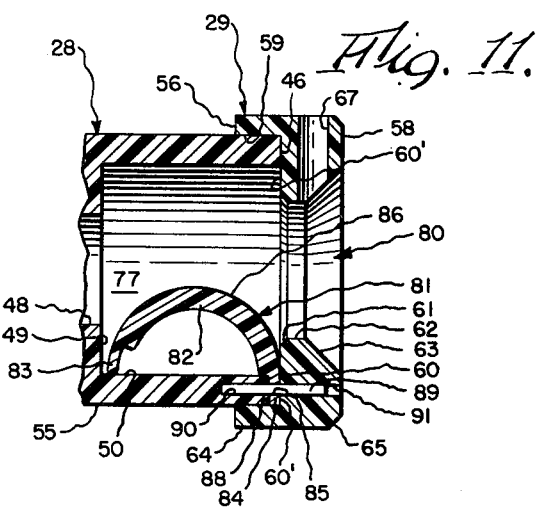
FIG. 11 is a fragmentary sectional view of the control valve, this view being generally similar to FIG. 10 but illustrating the flapper as having been moved away from the control opening during the inhalation mode.

Inhalation Mode (FIG. 11)

When the patient inhales, air will be inspired through the control opening 80 to cause the flapper to move away from the control opening to further expose or uncover the control opening and to permit such inhaled air to pass through control valve and enter the patient's lungs through the tracheal fistula.

Figure 12:
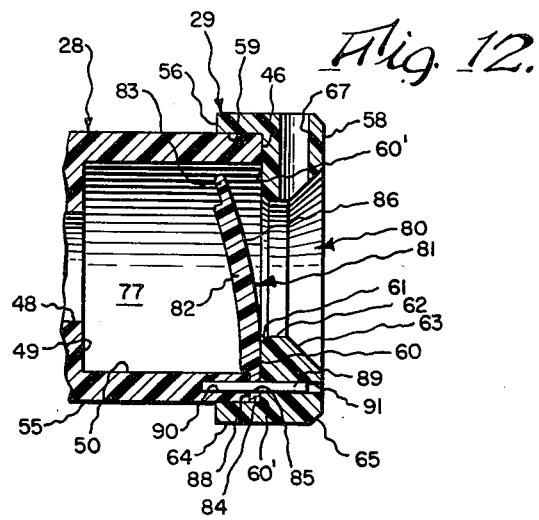
FIG. 12 is a fragmentary sectional view of the control valve, this view being generally similar to FIG. 10 but illustrating the flapper as having been displaced toward, but not covering, the control opening during the exhalation mode.

Exhalation Mode (FIG. 12)

When the patient exhales, expired air will enter the control valve 21 through the tracheal opening 78 and exit the control valve 21 through control opening 80 (FIG. 3). However, this outward flow of exhaled air will urge the flapper 81 to move from its normal position (FIG. 10) toward the seat and control opening. The force of this exhaled air on the flapper will be opposed by flapper spring portion 82 which prevents the flapper from fully closing the control opening during exhalation at normal pressures.

Figure 13:
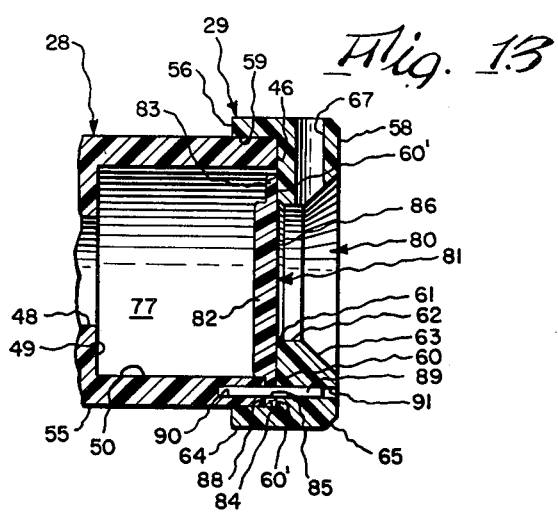
FIG. 13 is a fragmentary sectional view of the control valve, this view being generally similar to FIG. 10 but illustrating the flapper as having been moved toward the control opening to engage the seat during the talking mode.

Talking Mode (FIG. 13)

The patient may attempt alaryngeal speech by expiring air with a force sufficient to cause the flapper to move toward and engage the seat (FIG. 13), thereby closing the control opening and causing the flow of such expired air to be diverted through control valve diversion opening 79, to pass through flexible tube 23 and fitting 22, and enter the patient's hypopharyngeal cavity through the hypopharyngeal fistula. Thus, in the talking mode, the normal flow of exhaled air is diverted from the trachea, passed through the laryngeal prosthesis, and introduced into the hypopharyngeal cavity to enable alaryngeal speech by the patient.

Figure 14:
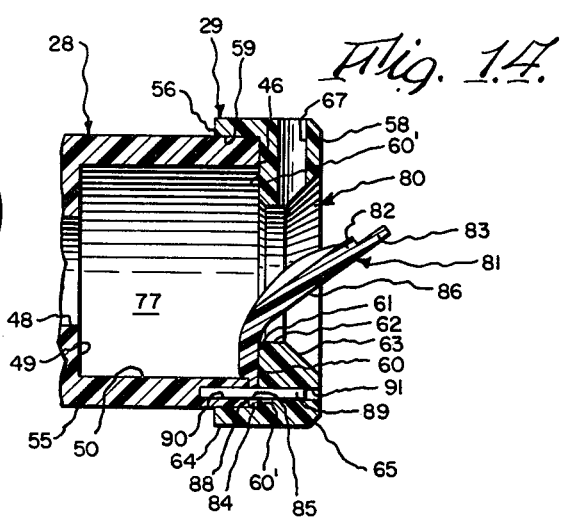
FIG. 14 is a fragmentary sectional view of the control valve, this view being generally similar to FIG. 10 but illustrating the flapper as having passed through the control opening during the coughing mode.

Coughing Mode (FIG. 14)

With respect to the laryngeal prosthesis, coughing is characterized by a relatively high pressure of exhaled air. This high pressure initially causes the flapper to move from its normal position (FIG. 10) to the talking position (FIG. 13) and, if such cough is of sufficient pressure, causes the flexible marginal portion 83 of the flapper to deform and enable the flapper to pass through the control opening (FIG. 14) to permit the exhaled air to pass through the control opening. When the cough has been completed, the spring portion 82 may be sufficient to urge the flapper to move back toward the control opening and, in cooperation with a subsequent attempt to inhale, to again deform flexible marginal portion 83 and pass through the control opening to reenter the chamber 77. In this regard, control valve inclined inner surface 61 acts as one inclined plane to facilitate outward passage of the flapper, and control valve inclined outer surface 63 acts as another inclined plane to facilitate reentry of the flapper into the control valve chamber 77. Obviously, the flapper may also be manually reset, if desired or necessary.

In this manner, the control valve 21 automatically enables the patient to inhale, exhale, and cough through control opening 80. Moreover, the laryngeal prosthesis 20 enables alaryngeal speech by the patient by selectively diverting exhaled air from the patient's trachea to the patient's hypopharyngeal cavity.

A high quality of alaryngeal speech may be obtained by using the laryngeal prosthesis 20 because expired air is diverted into the hypopharyngeal cavity to cause the lateral pharyngeal wall and the base of the tongue to vibrate. Sounds produced by such vibrations may appear more normal because of the proximity of the oral, nasal and pharyngeal naturally resonant cavities. Hence, the inventive prosthesis facilitates the rapid vocal rehabilitation of post-laryngectomy patients.

Figure 15:
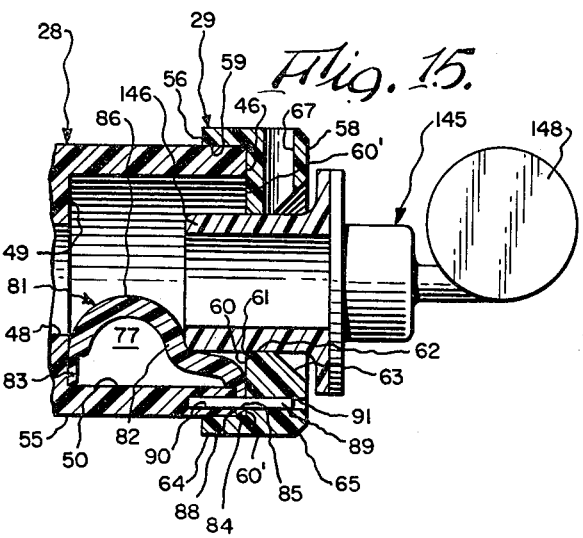
FIG. 15 is a fragmentary sectional view of the control valve, this view being generally similar to FIG. 10 but illustrating the plug portion of the audible device being inserted into the control opening to displace the flapper away from the control opening.

Audible Device (FIG. 15)

In FIG. 15, the prosthesis 20 is shown as further including an audible device, generally indicated at 145, which may be inserted into the control opening 80 to move or displace the flapper away from the control opening and to enable the patient to sound an audible signal. This audible device 145 is specifically shown as including a leftward tubular plug portion 146 which is adapted to fit within control opening 80, and a rightward conventional whistle portion 148, or other suitable device capable of producing an audible signal, operatively communicating with the control valve chamber through plug portion 146.

In the embodiment herein described, control valve intermediate part 28, nipples 68 and 95, control valve end cap 29, fitting end plug 94, and fitting body part 93 may be severally formed of a suitable acrylic plastic; control valve left end part 26, flapper 81, one-way valve 136, fitting mounting part 92, and the plug portion 146 of audible device 145 may be severally formed of silicone; flexible tube 23 may be formed of a silicone-coated dacron material; and pins 89 may be formed of stainless steel.

While the preferred embodiment has been illustrated and described as selectively communicating a tracheal fistula with a hypopharyngeal fistula to enable the patient to speak alaryngeally, it should be readily apparent that the laryngeal prosthesis may be employed to communicate the tracheal fistula with any other fistula leading into an alaryngeal body cavity, such as the cervical esophagus.

Moreover, the control valve 21 may be further utilized by a post-tracheotomy patient provided with a permanent tracheal fistula. These tracheotomy patients are normally able to inhale, exhale and cough directly through the tracheal fistula, but must manually close or cover this fistula when they desire to speak.

A tracheotomy patient may utilize the control valve 22 singly by permanently blocking or covering the diversion opening 79. With the modified control valve inserted into the tracheal fistula in the manner heretofore described, the tracheotomy patient may then inhale, exhale and cough directly through the control opening 80, and speak by exhaling air at a pressure sufficient to cause the flapper 81 to close the control opening 80 (FIG. 13). Hence, in the talking mode, the flapper automatically closes the control opening and enables the patient to speak without having to manually cover the tracheal fistula.

While a preferred embodiment of the invention has been shown and described, it will be understood by persons skilled in this art that various changes and modifications may be made without departing from the spirit of the invention which is defined by the following claims.

What is claimed is:

1. A laryngeal prosthesis for a laryngectomy patient provided with a tracheal fistula and a hypopharyngeal fistula and enabling alaryngeal speech by said patient, said prosthesis comprising:

a control valve having a housing defining a chamber therewithin and having a flapper, said housing being provided with a tracheal opening adapted to communicate said chamber with the trachea of said patient through said tracheal fistula, a diversion opening communicating with said chamber, and a control opening communicating said chamber with ambient atmosphere, a marginal portion of said housing about said control opening defining a seat facing into said chamber, said flapper being mounted on said housing in said chamber and having a flexible peripheral marginal portion, said flapper being adapted to move away from said control opening when said patient inhales, toward said control opening when said patient normally exhales, toward said control opening to cause said flapper marginal portion to sealingly assume the contour of said seat when said patient selectively exhales air with sufficient force, and to pass through said control opening by deformation of said flapper marginal portion when said patient coughs;

a fitting having an outlet opening adapted to communicate with the hypopharyngeal cavity of said patient through said hypopharyngeal fistula, and having an inlet opening communicating with said outlet opening; and means defining a conduit communicating said diversion opening with said inlet opening, whereby when said patient attempts to speak by such selective exhalation of air with sufficient force, said flapper moves toward said control opening to close same and to divert such flow of exhaled air through said fitting to said hypopharyngeal fistula to enable alaryngeal speech by said patient.

2. A laryngeal prosthesis according to claim 1 wherein said flapper includes a spring portion adapted to urge said flapper to assume an unbiased shape.

3. A laryngeal prosthesis according to claim 2 wherein said unbiased shape is arcuate.

4. A laryngeal prosthesis according to claim 2 wherein said spring portion is formed integrally with said flapper.

5. A laryngeal prosthesis according to claim 1 and further comprising:

a one-way valve arranged in said fitting and operative to permit a normal flow of such diverted exhaled air to pass through said fitting and enter said hypopharyngeal cavity but to prevent saliva from entering said conduit through said fitting.

6. A laryngeal prosthesis according to claim 1 wherein said housing is provided with at least one passageway arranged to communicate said ambient atmosphere with said control opening in the event that said control opening is externally closed.

7. A laryngeal prosthesis according to claim 1 and further comprising:

an audible device adapted to be inserted into said control opening to move said flapper away from said control opening to enable said patient to sound an audible signal.

8. A laryngeal prosthesis according to claim 1 wherein said seat is configured to have an inclined surface to facilitate such passage of said flapper therethrough.

9. A laryngeal prosthesis according to claim 1 wherein said housing is further provided with an inclined outer surface proximate said control opening to facilitate reentry of said flapper into said chamber.

10. A control valve for a tracheotomy patient provided with a trachael fistula and enabling said patient to automatically inhale, exhale, cough and talk without having to cover said trachael fistula, said control valve comprising:

a housing defining a chamber therewithin, said housing having a trachael opening adapted to communicate said chamber with the trachea of said patient through said trachael fistula and having a control opening communicating said chamber with ambient atmosphere, a marginal portion of said housing about said control opening defining a seat facing into said chamber;

a flapper mounted on said housing in said chamber and having a flexible peripheral marginal portion, said flapper being adapted to move away from said control opening when said patient inhales, toward said control opening when said patient normally exhales, toward said control opening to cause said flapper marginal portion to sealingly assume the contour of said seat when said patient selectively exhales air with sufficient force, and to pass through said control opening by deformation of said flapper marginal portion when said patient coughs;

whereby said patient may inhale, exhale and cough through said control opening, and may speak by selectively exhaling air at such force sufficient to cause said flapper to move toward and close said control opening.

11. A control valve according to claim 10 wherein said flapper includes a spring portion adapted to urge said flapper to assume an unbiased shape.

12. A control valve according to claim 11 wherein said unbiased shape is arcuate.

13. A control valve according to claim 11 wherein said spring portion is formed integrally with said flapper.

14. A control valve according to claim 10 wherein said seat is configured to have an inclined surface to facilitate such passage of said flapper therethrough.

15. A control valve according to claim 10 wherein said housing is further provided with an inclined outer surface to facilitate reentry of said flapper into said chamber.

* * * * *